United States Patent [19]

Slickers

[11] Patent Number: 4,592,655

[45] Date of Patent: Jun. 3, 1986

[54] METHOD OF DETERMINING ELEMENTS IN METALS BY MEANS OF OPTICAL EMISSION SPECTRUM ANALYSIS

[75] Inventor: Karl Slickers, Echandens, Switzerland

[73] Assignee: A.R.L. Applied Research Laboratories, S.A., Ecublens, Switzerland

[21] Appl. No.: 553,830

[22] Filed: Nov. 21, 1983

[30] Foreign Application Priority Data

Nov. 29, 1982 [DE] Fed. Rep. of Germany ....... 3244164

[51] Int. Cl.$^4$ ............................................ G01N 21/67
[52] U.S. Cl. .................................................. 356/313
[58] Field of Search ............... 356/300, 303, 306, 311, 356/313, 314, 326, 328

[56] References Cited

U.S. PATENT DOCUMENTS

| | | |
|---|---|---|
| 3,248,602 | 4/1966 | Irish et al. ........................... 356/313 |
| 3,729,259 | 4/1973 | Cooper et al. ....................... 356/311 |
| 3,876,306 | 4/1975 | Onodera et al. . | |
| 3,957,373 | 5/1976 | Clarke ................................ 356/313 |
| 4,326,801 | 4/1982 | Ono et al. ........................... 356/313 |

Primary Examiner—F. L. Evans
Assistant Examiner—Joel L. Harringa
Attorney, Agent, or Firm—Sandler & Greenblum

[57] ABSTRACT

Contents of elements in metals, e.g. aluminum in steel, which are present as a total quantity in an elemental/-dissolved form and in a non-elemental or separated form, are determined by sparking the surface of the metal under an inert atmosphere. The spectral signal is simultaneously measured as a function of time, and a signal is obtained which initially exhibits an intensity peak, from which the non-elemental or separated element content can be concluded, and the signal then stabilizes at a stationary value from which the total content ($C_t$) of element can be concluded. The elemental/dissolved proportion ($C_s$) can be concluded from the total area ($P_1$) below the peak, from the area ($P_2$) under the stationary intensity measured over a time ($t_2-t_1$) and from the total content ($C_t$).

10 Claims, 4 Drawing Figures

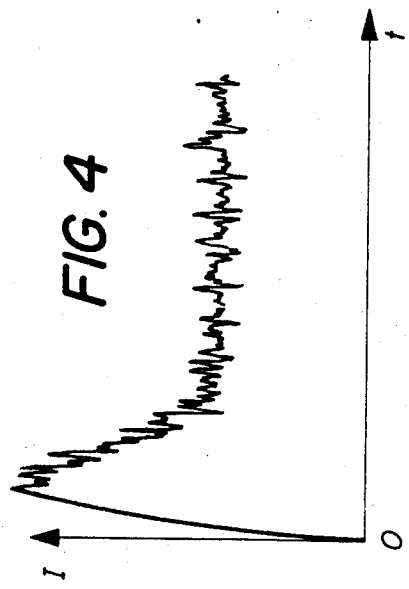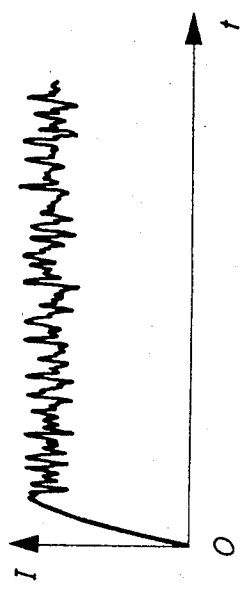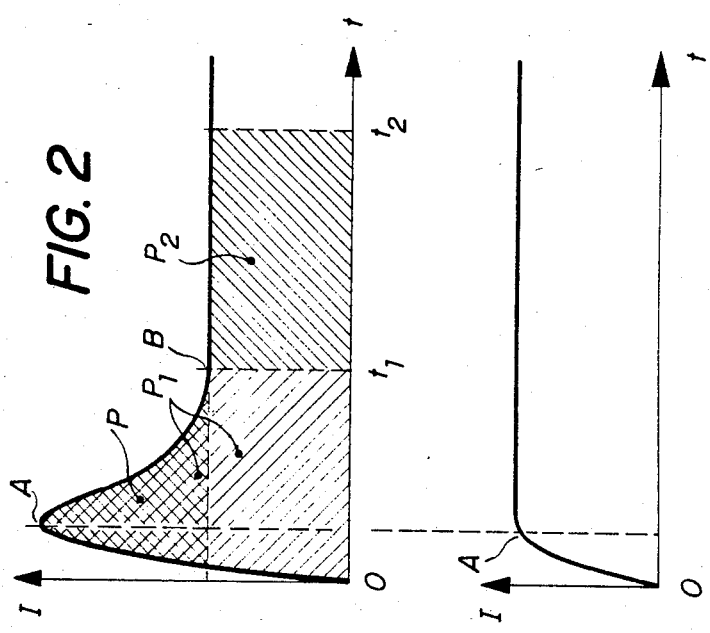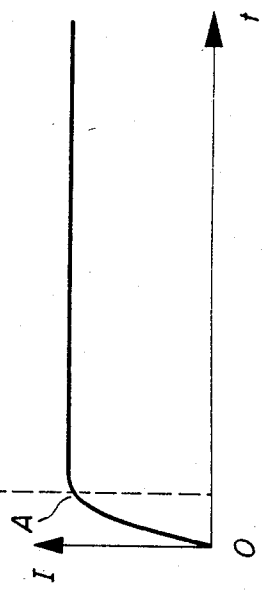

METHOD OF DETERMINING ELEMENTS IN METALS BY MEANS OF OPTICAL EMISSION SPECTRUM ANALYSIS

This invention relates to a method of determining contents of elements in metals, for example in steel, in particular the total amount of elemental and non-elemental proportions. The case of aluminium in steel is used as an example.

Where steel is concerned, there is the risk that gases may evolve. Oxygen reacts with carbon and forms carbon monoxide. Thus, inclusions of gas are produced which have an adverse effect on the mechanical properties of steel.

In order to bind the oxygen and to prevent a reaction with the carbon, metallic elements (deoxidizing agents), for example aluminium are added to the steel. The aluminium reacts with the oxygen and forms aluminium oxide ($Al_2O_3$) which is insoluble (metallurgically inactive). On the other hand, elemental aluminium is soluble in steel and is metallurgically active. Too great a content of deoxidizing agent is detrimental to the quality of the steel. Therefore, a quantity of aluminium has to be added which is certainly slightly more than that which is just sufficient to bind all of the free oxygen, but on the other hand, is not so great that it could impair the quality of the steel.

This invention provides a method which allows a continuous and almost direct control of the total content and of the elemental and non-elemental proportions. Immediate results cannot be obtained by conventional methods, for example by chemical analysis. Other methods, electrochemical methods or X-ray spectrochemistry, have not been developed technically to such an extent that they could be used for this purpose as a matter of course.

The method which is proposed in the present invention is distinguished in that the surface of the metal is sparked under an inert atmosphere and the spectral signals which are emitted are simultaneously measured as a function of time. Recordings are obtained which initially exhibit an intensity peak. This peak indicates the non-elemental/separated part. The recordings then stabilize at stationary final values (intensities in the stationary spark-off condition) which indicate the total content of the elements. The elemental/dissolved part $C_s$ is concluded from the total area ($P_1$) below the peak, from the area ($P_2$) under the stationary intensity which is measured over a time ($t_2-t_1$) and from the total content ($C_t$). In general, $t_2-t_1$ is of an order of magnitude corresponding to $t_1$. Preferably $t_1$ equals $t_2-t_1$.

It is possible to analyse several elements using this method by selecting several spectral lines. When several elements are to be analysed, as many recordings are made as spectral lines have been selected. The size of the area below the peak is proportional, in an adequate approximation, to the quantity of insoluble element, within a broad standard range. The constant final value gives the total quantity of the element. The ratio of the area below the constant final value which is measured over a time ($t_2-t_1$) to the contents of the area below the peak is, in adequate approximation, a value which may be used to calculate the elemental (dissolved) part.

It is possible to measure either the absolute intensities of the spectral lines which have been selected or the ratios of these intensities to those of other suitable spectral lines.

This method of determination may be used for all elements in metals, for example for aluminium in steel, or for boron, silicon, titanium, zirconium, calcium, etc.

The present invention will now be described in more detail in the following description and drawings, for example using the determination of aluminium.

FIG. 1 shows a recording of the intensity I for aluminium, in which all the aluminium is present in elemental (dissolved) form, and FIG. 2 shows the recording which is obtained when aluminium is present in an elemental and nonelemental form.

FIGS. 3 and 4 are unsmoothed curves corresponding to FIGS. 1 and 2 respectively.

For reasons of clarity, these first two curves (also termed spark-off curves) are produced by smoothing actual curves, for which examples are given in FIG. 3 (corresponding to FIG. 1) and in FIG. 4 (corresponding to FIG. 2).

In FIG. 1, the intensity I of the spectral line is plotted vertically (as the ordinate) as a function of the time t. It may be seen that the curve initially rises to a point A. The time between the beginning and the projection of point A on the abscissa is the spark-in time. Thereafter, the curve stabilizes over a plateau, termed the stationary or constant final value, from which is possible to conclude the total content of aluminium in the steel sample.

The point A reoccurs in FIG. 2 and it corresponds to the end of the spark-in time. Thereafter, the curve falls to a point B, the beginning of the stationary condition. The time span between A and B is the time which the sample needs for homogenization at the focus. The surface of the sample is melted to a depth of from 30 to 50 microns, so that the sparked surface becomes homogeneous and emits a signal which corresponds to the stationary final value.

The size P of the area below the peak which is delimited by the constant final value is proportional to the non-elemental part of the aluminium which is present. It may be considered as the difference between the total area $P_1$ below the peak and the area $P_2$ which corresponds to the stationary final value. The area $P_2$ corresponds to the integrated stationary final value over the time $t_2-t_1=t_1$ (FIG. 2). The total content $C^t$ of aluminium is proportional, in an adequate approximation, to the integrated intensity in the stationary condition (area $P_2$). The ratio of the integrated intensities in the stationary spark condition (area $P_2$) and of the total area $P_1$ below the peak produces a factor F. Multiplying the total content by F gives the elemental part $C_s$. On account of the inhomogeneous distribution of the non-elemental part, the amount of non-elemental metal may be calculated more effectively as the difference between the total content and the elemental part.

As may be established, these measurements are immediate and they allow instantaneous intervention in the production process. In a typical case, the spark times last for about 15 seconds.

Supercritically damped discharges under an argon atmosphere are used. When determining aluminium in steel, a spectral line having a wavelength of 394.4 nm is of particular interest. In the case of boron, for example, a spectral line having a wavelength of 182.64 nm would preferably be used.

As has already been mentioned, FIGS. 3 and 4 show what actual recordings look like.

FIG. 3 corresponds to a total content of aluminium of 540 ppm with a non-elemental content of less than 20 ppm, whereas FIG. 4 corresponds to a total aluminium content of 560 ppm with a non-elemental content of 200 ppm.

I claim:

1. A method of determining contents of elements in metals which are present as a total quantity in an elemental/dissolved form and in a non-elemental or separated form, which comprises sparking the surface of the metal under an inert atmosphere, and simultaneously measuring the spectral signal as a function of time, said signal which is obtained initially exhibiting an intensity peak, from which said non-elemental or separated element content is concluded, and said signal then stabilizing at a stationary value from which the total content ($C_t$) of said element is concluded, and said elemental/dissolved proportion ($C_s$) is concluded from the total area ($P_1$) below the peak, from the area ($P_2$) under the stationary intensity measured over a time ($t_2-t_1$) and from the total content ($C_t$).

2. A method according to claim 1, in which a given spectral line is selected for recording in order to determine the content of a single element.

3. A method according to claim 1, in which several spectral lines are selected, each of which gives a recording in order to simultaneously determine the contents of several elements.

4. A method according to claim 3, in which either the absolute intensities of the selected spectral lines, or the ratios of these intensities to those of other suitable spectral lines are measured.

5. A method according to claim 1, in which the proportion ($C_s$) of the elemental/dissolved element having a ratio F of the area ($P_2$) under the stationary final value to the total area ($P_1$) under the peak is calculated in the form of the metallic proportion ($C_s$)=F×total content ($C_t$).

6. A method according to claim 1, in which within a broad standard range, the content of the non-elemental or separated element is calculated in a sufficient approximation as being proportional to the area (P) below the peak which is delimited by the stationary final value.

7. A method according to claim 1, in which the total quantity ($C_t$) of one element is calculated in a sufficient approximation as being proportional to the integrated stationary final value.

8. A method according to claim 1, in which the content of the non-elemental or separated element is calculated from the total area ($P_1$) below the peak and from the area ($P_2$) which corresponds to the stationary final value.

9. A method according to claim 1 in which the content ($C_s$) of the elemental/dissolved element is calculated as the difference between the total content ($C_t$) and the non-elemental proportion.

10. A method according to claim 1, in which the elements to be measured are selected from the group of elements which are present in metals partly in an elemental/dissolved form and partly in non-elemental or separated form.

* * * * *